(12) United States Patent
Mulder

(10) Patent No.: US 7,651,468 B2
(45) Date of Patent: Jan. 26, 2010

(54) UROLOGICAL INSTRUMENT FOR ASSESSING A URINE FLOW

(75) Inventor: Karel Hero Mulder, Delft (NL)

(73) Assignee: IQ + Investments N.V., Curacao (AN)

( * ) Notice: Subject to any disclaimer, the term of this patent is extended or adjusted under 35 U.S.C. 154(b) by 275 days.

(21) Appl. No.: 10/734,274

(22) Filed: Dec. 15, 2003

(65) Prior Publication Data

US 2004/0243074 A1 Dec. 2, 2004

(30) Foreign Application Priority Data

Dec. 13, 2002 (NL) .................................. 1022161

(51) Int. Cl.
*A61B 5/00* (2006.01)
*B65D 81/00* (2006.01)
(52) U.S. Cl. ....................... 600/580; 600/573; 600/584
(58) Field of Classification Search ......... 600/573–574, 600/580, 584; 604/317–318, 327–331, 349
See application file for complete search history.

(56) References Cited

U.S. PATENT DOCUMENTS

| | | | | |
|---|---|---|---|---|
| 2,856,932 A * | 10/1958 | Griffitts | ...................... | 604/171 |
| 3,831,446 A * | 8/1974 | Dye | ............................. | 73/861 |
| 3,831,453 A * | 8/1974 | McWhorter | ................... | 73/427 |
| 3,871,231 A | 3/1975 | Ciarico | | |
| 3,928,875 A * | 12/1975 | Persson | .......................... | 4/451 |
| 4,296,502 A * | 10/1981 | Bortle | ......................... | 4/144.1 |
| 4,532,936 A * | 8/1985 | LeVeen et al. | .............. | 600/575 |
| 4,753,249 A * | 6/1988 | Muller | ........................ | 600/584 |
| 4,865,046 A | 9/1989 | Duran | | |
| 4,886,509 A * | 12/1989 | Mattsson | ..................... | 604/349 |
| 5,111,539 A * | 5/1992 | Hiruta et al. | ................... | 4/661 |
| 5,423,792 A * | 6/1995 | Oxley | ......................... | 604/409 |
| 5,605,161 A * | 2/1997 | Cross | ......................... | 600/584 |
| 6,346,097 B1 * | 2/2002 | Blaney | ........................ | 604/327 |
| 6,530,909 B1 * | 3/2003 | Nozaki et al. | ............... | 604/349 |
| 2002/0193762 A1 * | 12/2002 | Suydam | ...................... | 604/327 |

* cited by examiner

*Primary Examiner*—Max Hindenburg
*Assistant Examiner*—Helen Nguyen
(74) *Attorney, Agent, or Firm*—Young & Thompson

(57) ABSTRACT

A urological instrument (1) for assessing a urine flow, includes a receiving member (5) for the urine flow which, at least during operation, is in open liquid communication with a urine guide (6). The urine guide (6) leads to an inlet of flow indicator element (7) for assessing at least a magnitude of the urine flow. The receiving member (5) has a first, relatively compact storage state and a second, expanded ready-to-use state and is designed and adapted to allow it to be brought manually from the storage state to the ready-to-use state. At least in the ready-to-use state the receiving member comprises a cavity open on at least one side for receiving the urine flow therein.

18 Claims, 4 Drawing Sheets

UROLOGICAL INSTRUMENT FOR ASSESSING A URINE FLOW

Figure 1:
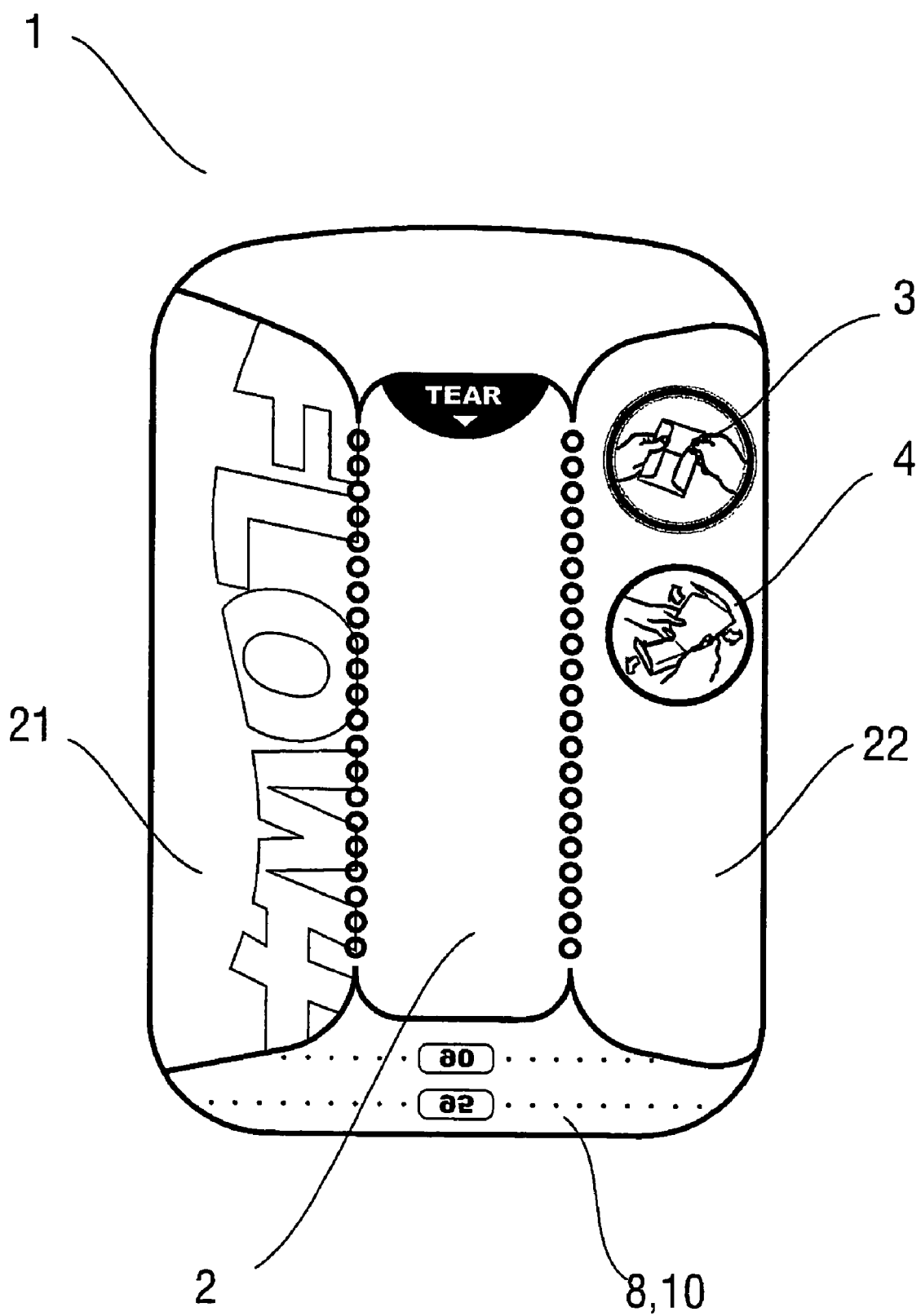

The invention relates to a urological instrument for assessing a urine flow, comprising a receiving member for the urine flow which, at least during operation, is in open liquid communication with a urine guide and an inlet of flow indicator means for assessing at least a magnitude of the urine flow. The magnitude of the urine flow is here understood to mean the possibly varying force or speed with which the urine flow enters the instrument.

Such an instrument is known from the Netherlands patent NL-A-1015080. The known instrument is embodied with a funnel-like receiving member to which the urine guide connects. This urine guide can have an outflow opening on its underside. The flow indicator means are formed in the known device by a side wall of the guide which is provided with a number of regularly distributed outflow openings. Outflow from of these openings is representative of the flow rate of the admitted urine flow.

A drawback is that the practical usefulness of the known instrument in a modern hospital environment or in the environment of the individual patient is not on a par with the simplicity of the known instrument and the low cost at which this latter can be manufactured. A further drawback of the known instrument is that it only provides a measurement of the magnitude of the urine flow and gives no information about other medically relevant parameters, such as for instance the total quantity of the admitted urine flow.

The invention has for its object, among others, to obviate these problems of the known instrument and achieve advantages which will become apparent from the following.

In a first aspect of the invention, the urological instrument is characterized for this purpose in that the receiving member has a first, relatively compact storage state and a second, expanded ready-to-use state, that the receiving member is designed and adapted to allow it to be brought manually from the storage state to the ready-to-use state, and that at least in the ready-to-use state the receiving member is open on at least one side and comprises a cavity for receiving the urine flow therein. In the storage state the instrument can thus be relatively compact and convenient as a whole so that it can be easily carried by a user and kept in stock. In order to be used the instrument can then be brought relatively easily and manually into a ready-to-use state by expanding at least the receiving member. Then present therein is a cavity open on at least one side for receiving the urine flow therein.

In a first preferred embodiment the instrument according to the invention is characterized in that a collecting device is provided therein which, at least during operation, is in open communication with an outlet of the flow indicator means, that the collecting device is provided with a closing member normally in the closed position and that the collecting device is expandable from a relatively compact storage state to an expanded position of use. Owing to the presence of the collecting device the instrument can also be applied in situations where a sewer system or other drain is not immediately available. By operating the closing member the collecting device can be emptied afterwards at an appropriate moment or suitable location. Because the collecting device is expandable, the above stated convenience of use and compactness of the instrument is not adversely affected, or hardly so, at least in the storage state. A further particular embodiment of the instrument herein has the feature according to the invention that the collecting device comprises a collecting bag. It has been found possible in practice to integrate such a collecting bag in the instrument in exceptionally simple manner without detracting from the compactness of the device in the storage state. During use the bag expands as it becomes further filled with urine.

A further preferred embodiment of the instrument has the feature according to the invention that the collecting device is provided with volume indicator means for a urine volume received therein. Not only can the flow rate and magnitude of the urine flow be readily measured in this way, but it is also possible to measure the quantity of urine serving as basis for the measurement to be carried out with the instrument. After measurement of this quantity of the urine flow, the collected urine can be removed from the collecting device by operating the closing member.

In a specific embodiment the instrument according to the invention has the feature that there is connected to the urine guide on an end opposite the receiving member a collecting bag for the urine which is provided with a closing member normally in the closed position, and which collecting bag is provided with second indicator means for the quantity of the urine flow.

In a further aspect of the invention the instrument has the feature that the instrument is embodied as a disposable article which is formed substantially from flexible material and which is in folded position at least in the storage state. Such an instrument embodied as disposable means is very suitable for use in a modern environment such as a professionally equipped hospital. The instrument embodied in this manner is moreover very suitable for home use. After using the instrument to measure the amount and optionally the quantity of the urine flow, the instrument can be discarded with the hospital waste or the domestic refuse. In a particularly practical embodiment, the instrument herein has the feature that one or more components of the instrument lie at least substantially folded onto each other in the storage state and at least substantially mutually in line in the ready-to-use state. In the ready-to-use state the urine flow can flow along an almost straight urine path through the instrument, while the folded storage state provides the desired compactness. The urological instrument according to the invention can herein be suitably embodied such that in the storage state at least one of the receiving member and the collecting device covers the urine guide on one side of the flow indicator means.

The instrument according to the invention can be produced on large scale in relatively economic manner. A particularly practical embodiment of the instrument according to the invention has for this purpose the feature that the flexible material comprises at least two foil sheets joined hermetically to each other on a mutual contact surface while at least partially forming one or more components of the instrument. By glueing or sealing two separate foil sheets for instance locally to each other, the one or more components of the instrument can be simultaneously formed therefrom in the same processing step. In respect of these components a further embodiment of the instrument relates more particularly to one or more of the components including the receiving member, the urine guide, the flow indicator means and the collecting device.

In a further particular embodiment, the device according to the invention has the feature that the flow indicator means comprise a separate measuring device enclosed between the two foil sheets. The measuring device can thus be manufactured separately with the desired precision and optionally calibrated. The less critical parts of the device, such as the receiving member, the urine guide and optionally the collecting device, can then be formed directly by the two foil sheets without loss of precision.

So as to be able to ensure reliable and reproducible measurements, a further preferred embodiment of the instrument according to the invention has the feature that it is provided with an irreparable breakable seal for holding the instrument in the storage state, and that only after breaking of the breakable seal can the instrument be brought into the ready-to-use state.

Particularly when the instrument is used in the home situation, i.e. by the end user himself, the quality of the measurement stands or falls with the discipline with which the obtained measurement data are recorded and collected. With a view hereto, a further preferred embodiment of the instrument according to the invention has the feature that recording means are arranged on an outer side thereof for manual recording of one or more indicator values determined with the instrument. More particularly the instrument herein has the feature that the recording means comprise a removable self-adhesive label. The measured values obtained can in this case be recorded in simple manner on the device itself. The final analysis and diagnosis will normally be left to a doctor. The latter obtains the measurement data in the form of one or more thus completed labels. In the stated self-adhesive embodiment, this is possible in very practical manner by detaching the self-adhesive label from the instrument and affixing it at a location reserved for the purpose, for instance in a logbook to be kept.

A further particular embodiment of the instrument has the feature according to the invention that the label is arranged at the position of the flow indicator means and leaves a transparent window at the position of a display area of the flow indicator, means. The label can thus also serve as optionally informative framing of the flow indicator means.

An indication of the chemical composition of the urine flow may also be desirable in some cases in addition to or instead of one or more of the above stated measurement data. In order to also provide this, a further preferred embodiment of the instrument according to the invention has the feature that urine indicator means are provided at least locally in a urine path through the instrument in order to determine at least one component of the composition of the urine flow, and more particularly that the urine indicator means comprise a flexible carrier, in particular paper, which is provided with a suitable indicator substance. Such indicator means are per se available to a skilled person and can thus be integrated in simple manner into the instrument according to the invention. In a more specific embodiment this involves determining one or more urine components from a group of glucose, bilirubin, ketones, blood, proteins, urobilinogen, nitrites, leucocytes and acids.

With a view to the final diagnosis to be made, it is also desirable in some cases to have information available about the total urination time of the patient. In order to provide this a further preferred embodiment of the instrument according to the invention has the feature that time duration indicator means are provided therein for determining a time duration of the urine flow. In a particular embodiment the instrument according to the invention is herein characterized in that the time duration indicator means comprise a reservoir which at least during use is in open communication via a defined passage opening with the urine flow and that the reservoir is provided with volume indicator means for a urine volume received therein. The defined passage opening allows through a more or less fixed quantity of urine per unit of time. The total volume received in the reservoir is therefore a measure of the time duration of the liquid communication with the urine flow, i.e. the duration of urination. In a further particular embodiment, the instrument according to the invention herein has the feature that the passage opening is situated at least close to an inlet of the flow indicator means. This embodiment is here based on the insight that, among other parts, the outlet of the flow indicator means will be continuously supplied with the urine flow during use.

Figure 2:
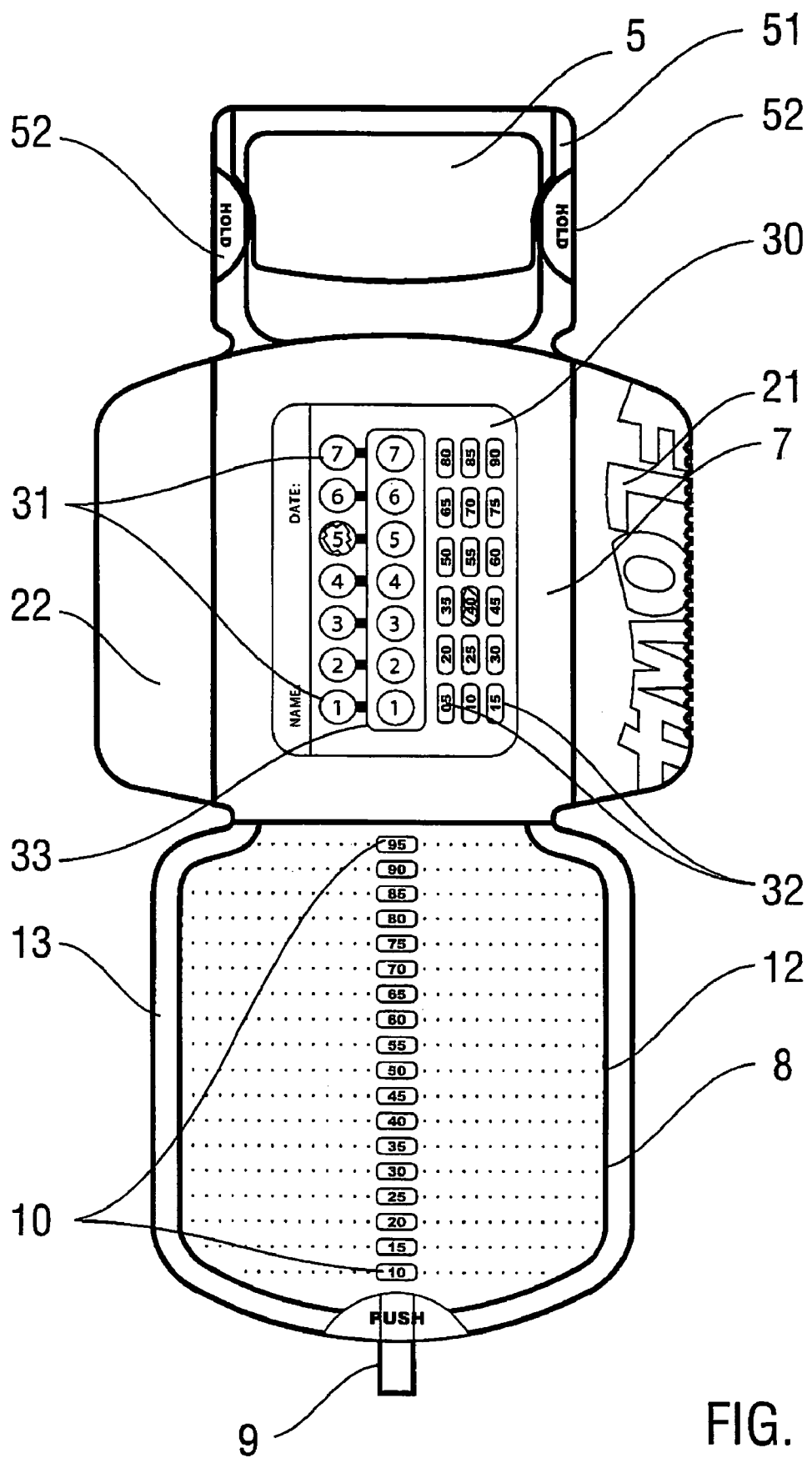
Figure 3:
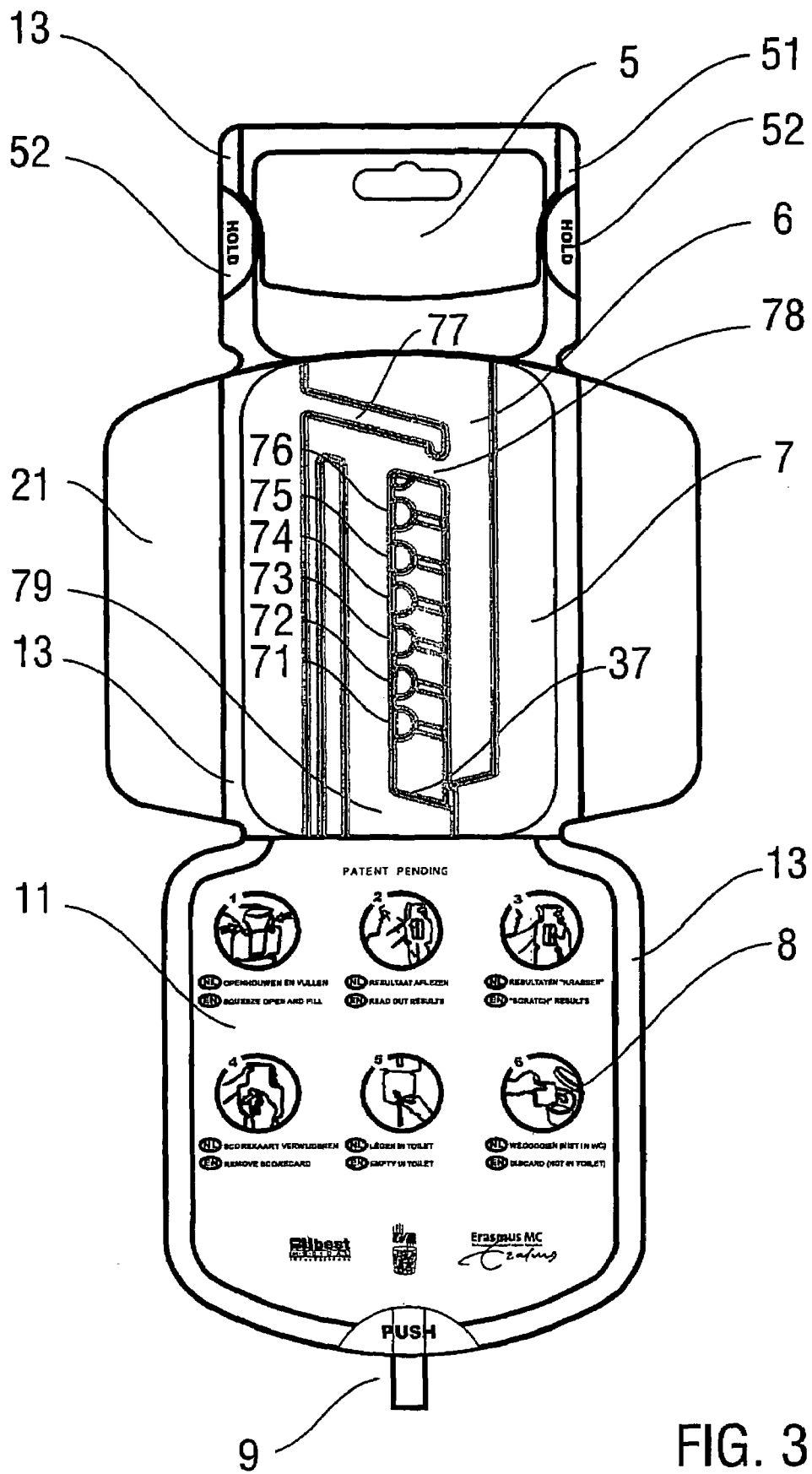
Figure 4:
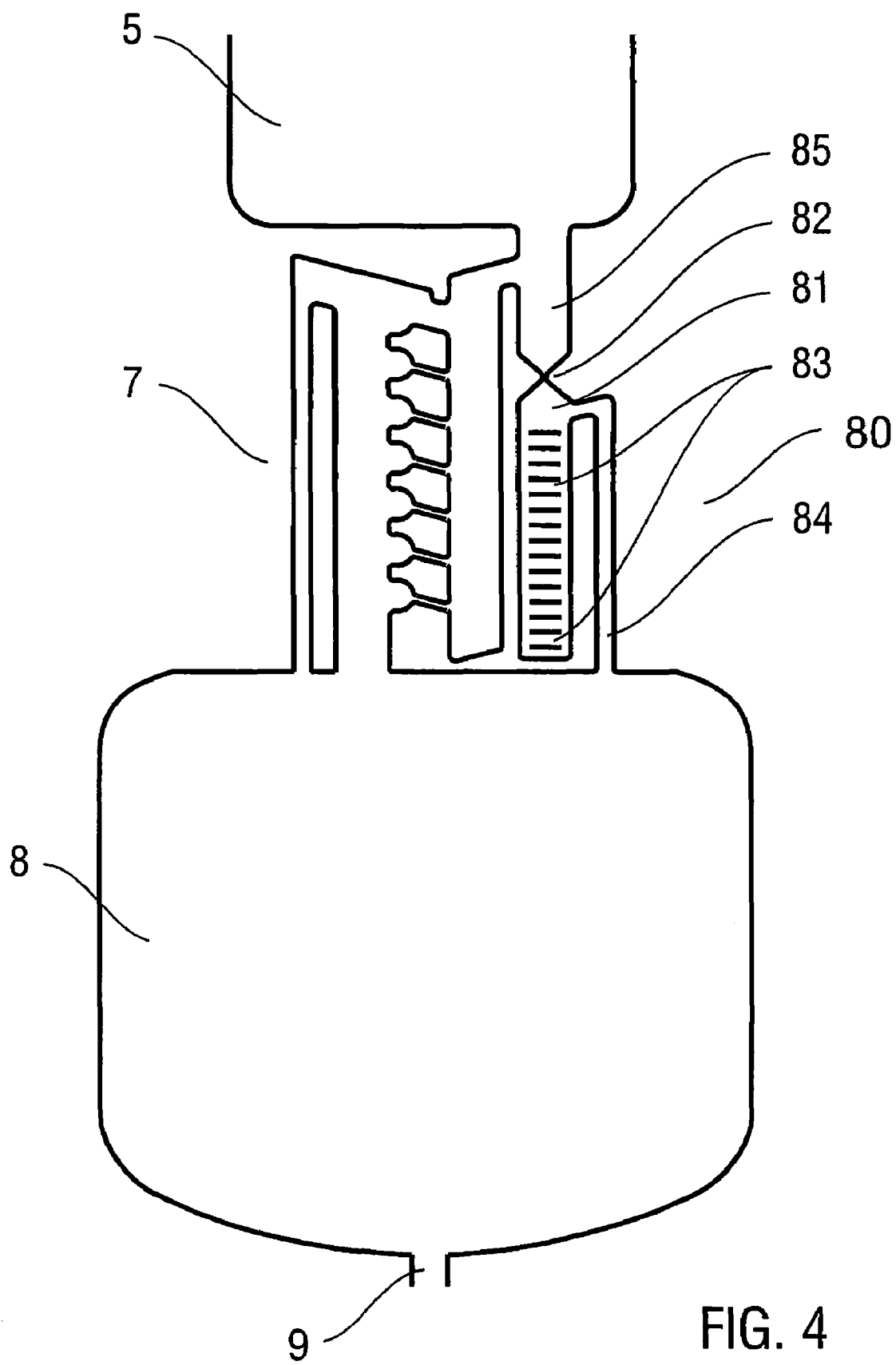

The invention will be further elucidated hereinbelow with reference to a number of exemplary embodiments and an associated drawing. In the drawing:

FIG. 1 shows the urological instrument according to the invention in the storage position, FIG. 2 shows the urological instrument according to the invention in the ready-to-use state from the front, FIG. 3 shows the urological instrument according to the invention in the ready-to-use state from the rear, and FIG. 4 shows a part of a second embodiment of an instrument according to the invention having time duration indicator means integrated therein.

The figures are herein purely schematic and in any case not always drawn to the same scale. Some dimensions in particular may be exaggerated to a greater or lesser extent for the sake of clarity. Corresponding parts are designated as far as possible in the figures with the same reference numeral.

Referring to FIG. 1, an exemplary embodiment of the urological instrument 1 according to the invention is shown in a storage state, wherein different parts of the instrument are folded up in relatively compact manner. Instrument 1 is provided with an irreparable breakable seal in the form of a tear-off strip 2 which, together with two side pieces 21, 22 arranged on either side, hold the whole article together. After removal of this tear-off strip 2 the urological instrument 1 can be brought into the ready-to-use state by unfolding the parts as the user is shown with graphic instructions 3 and 4, so-called pictorials, arranged for this purpose. The ready-to-use state is further shown in FIGS. 2 and 3. Shown in these figures is that as soon as the instrument 1 is brought from the folded-up storage state shown in FIG. 1 to the unfolded ready-to-use state, the different components thereof lie mutually in line.

The instrument shown here is embodied as a disposable article formed almost wholly from flexible material. For manufacture of the instrument use is made here of two identically shaped foil sheets 11,12 which are placed into contact with each other while enclosing a strengthening edge or insert 13 of cardboard, plastic or other suitable, relatively rigid and resilient material. The foil sheets are herein joined hermetically to each other on their contact surface by sealing thereof at an increased temperature and pressure as according to a defined sealing pattern, which pattern defines a receiving member 5, a urine guide 6, flow indicator means 7 and a collecting device 8 between the two foil sheets.

For the purpose of its measuring function the instrument 1 comprises a receiving member 5 at the top for receiving the urine flow on which a magnitude measurement of the flow rate and a quantity measurement has to be performed. In the storage state the receiving member 5 is relatively flat and folded together with the other components to form a compact package. The strengthening part 51 arranged at the position of the receiving member comprises two pressure points 52 with which the receiving member can be opened to the ready-to-use state by manually exerting an appropriate pressure thereon. In this situation receiving member 5 comprises a cavity which is open on a top side to receive the urine flow therein.

This receiving member 5 takes an open form on the underside and debouches into a urine guide 6 which is provided with the flow indicator means 7 which are shown in FIG. 2 and serve to enable assessment of a magnitude of the urine flow. The flow indicator means 7 comprise a number of outflow openings and side channels 71-77 of urine guide 6 which have been defined in the sealing pattern of the two foil sheets.

Via a part of urine guide 6 an inlet 78 of a measuring device is in open communication with the open underside of receiving member 5 in order to collect the received urine flow, while the urine flow can leave the measuring device at an outlet 79.

Via urine guide 6 the urine flow runs through the measuring device via one or more of the outflow openings and side channels 71-77 to the outlet 79 thereof. As the figure shows, the outflow openings 71-77 arranged in the side wall of the urine guide are arranged at mutually differing heights as seen from a bottom. The greater, i.e. stronger, the magnitude of the urine flow, the higher the urine column that will occur at the position of the measuring device in urine guide 6, so that as seen from the bottom urine can leave the device via more outflow openings and side channels 71-77. Channels 71,72 herein rise with a slight inclination, as seen in the flow direction, to prevent the possibility of the urine flow flowing prematurely therethrough, which would otherwise adversely affect the measuring result. Not further shown, but wholly clear to the skilled person, is that the outflow openings 71-77 placed in the side wall can be provided with for instance indicator paper or ether recording means, such as a float system or an electronic recording circuit so as to make outflow of urine therethrough more readily visible if desired. The number of outflow openings through which flow thus occurs is a measure for the magnitude of the received urine flow.

The shown embodiment comprises instrument 1 according to the invention in a relatively simple form, i.e. with outflow openings 71-77 which all have the same diameter and which are moreover distributed in regular arrangement in urine guide 6. It will be apparent that diverse variants hereof can be envisaged to meet practical requirements, i.e. in order for instance to linearize the instrument, wherein the outflow from a higher outflow opening 71-77 corresponds in each case to an equal increase in the inflow rate into instrument 1.

Instrument 1 allows of simple use in practice by for instance placing instrument 1 obliquely in a measuring beaker in which the urine which has flowed out via outflow openings 71-77 can be collected. This measuring beaker then also provides a measure for the quantity of released urine. In the present embodiment however, use is made of an embodiment wherein a collecting device 8 provided with volume indicator means 10 is already incorporated in the instrument itself. The collecting device here comprises a collecting bag defined in the sealing pattern of the two foil sheets. Collecting bag 8 connects onto the urine guide 6 at the end opposite receiving member 5 for receiving the urine with which the above mentioned flow rate measurement (magnitude) of the urine flow has taken place. In the storage state the collecting bag 8 is folded together with the rest of the instrument and herein covers the urine guide at the position of the measuring device. Collecting bag 8 is preferably provided on its underside with a closing member 9 which is normally in the closed position. Collecting bag 8 can be emptied by operating this closing member 9.

FIG. 2 further shows that collecting bag 8 is provided on its front side with a content measurement indication 10 which thus forms volume indicator means for determining the total quantity of the urine flow. On a front side of instrument 1 are situated recording means in the form of a removable self-adhesive label 30 on which the possible measured values 31, 32 of both the magnitude measurement and the volume measurement are preprinted. The correct respective values are recorded in reliable manner by marking the values thereon. Label 31 can be easily detached after use of the instrument and be adhered in a logbook or onto another suitable carrier so as to be made available to the doctor treating the case. Label 30 is also provided with a transparent window 33 at the position of a display area of flow indicator means 7 so as not to adversely affect the legibility thereof. The label thus also provides an informative framing of this display area.

From the above elucidation it will be apparent that instrument 1 is preferably embodied as disposable article, wherein it is advantageous that it be formed substantially from flexible material. This provides the option that, from the storage state shown in FIG. 1, in which receiving member 5, the urine guide and collecting bag 8 are folded onto each other, the urological instrument 1 can be readily brought to the ready-to-use state shown in FIGS. 2 and 3, in which these components are placed mutually in line. With a view to a possibly desired greater measurement accuracy, a separate measuring device can if desired be applied for the flow indicator means, wherein use can be made of substantially the same configuration. This can in particular be an injection moulded article or otherwise manufactured body which can be produced with a high degree of reproducibility within precise dimensional tolerances. This measuring device can then be enclosed and sealed together with strengthening edge 51 between the two foil sheets during manufacture of instrument 1.

FIG. 4 shows a relevant part of a second exemplary embodiment of the instrument according to the invention which is otherwise substantially the same as the first embodiment. In this case the instrument is also provided with time duration indicator means 80 integrated therein for determining a time duration of the urine flow. The time duration indicator means 80 herein comprise a reservoir 81 which, via a defined passage opening 82, is in open communication with urine guide 6 and the urine flow therethrough. Reservoir 81 and passage opening 82 are defined by the sealing pattern of the two foil sheets from which the instrument has been formed, although, similarly to the flow indicator means 7, they can if desired also be embodied as separate device and be enclosed between the two foil sheets for the purpose of for instance an optionally desired greater precision. A buffer reservoir 85 preceding the passage opening 82 ensures an uninterrupted time measurement in the event of a briefly faltering urine flow.

The passage opening is situated close to inlet 78 of flow indicator means 7, i.e. close to the outflow opening of the receiving member, so that during operation of the instrument the reservoir 81 is being continuously supplied from the urine flow. During the whole of the urinating time the defined passage opening 82 herein allows through a more or less fixed quantity of liquid per unit of time, so that the total volume collected in the reservoir is a measure for the time duration of the urine flow, and therefore the urination time. Reservoir 81 is provided with a suitable measurement indication, for instance in the form of an appropriate imprint. The stated conversion from volume to time duration can if desired already be calculated in the measurement indicator 83 so that the time duration can be read off directly. A venting channel 84 ensures that during operation air can escape freely out of reservoir 81 as it fills with urine.

Although the invention has been elucidated above with reference to only two exemplary embodiments, it will be apparent that the invention is by no means limited thereto. On the contrary, many variations and embodiments are still possible for a person with ordinary skill in the art without requiring him to depart from the scope of the invention.

It is expressly noted that the scope of protection arising from the following claims is defined solely by the content of these claims to the extent they relate to the essence of the invention as can be found in the foregoing description, the drawings or the grant documents.

The invention claimed is:

1. A urological measuring instrument for determining a magnitude of urine flow, the instrument comprising:
a receiving member for receiving the urine flow; and
a urine guide in communication with the receiving member, comprising an inlet and an outlet for the urine flow, the urine guide further comprising a flow indicator for measuring the magnitude of the urine flow, the flow indicator in communication with the inlet and the outlet,
wherein the instrument has a compacted storage state and an expanded ready-to-use state, and in the compacted storage state the receiving member, urine guide, and flow indicator are substantially folded onto each other with respective external surfaces facing each other and are substantially flush with each other, and in the ready-to-use state, the receiving member is open on at least one side, comprises a cavity for receiving the urine flow therein, and is in liquid communication with the inlet of the urine guide, and
the flow indicator comprises a plurality of outflow openings and side channels arranged in a side wall of the urine guide through which the urine flow occurs, whereby the number of the outflow openings through which the urine flow occurs is a measure of the magnitude of the urine flow.

2. The instrument according to claim 1, further comprising a collecting device, wherein at least in the expanded ready-to-use state, the collecting device is in liquid communication with the urine guide on an end opposite the receiving member, the collecting device comprises a closing member having a normally-closed position, and the collecting device is expandable from the compacted storage state to the expanded ready-to-use state.

3. The instrument according to claim 2, wherein the collecting device is connected to the outlet of the urine guide.

4. The instrument according to claim 2, wherein the collecting device comprises a collection bag.

5. The instrument according to claim 2, wherein the collecting device further comprises a volume indicator for measuring a urine volume received therein.

6. The instrument according to claim 2, wherein in the compacted storage state at least one of the receiving member and the collecting device covers the urine guide on one side of the flow indicator.

7. The instrument according to claim 1, further comprising an irreparable breakable seal adapted to hold the instrument in the compacted storage state and allowing the instrument to be brought into the expanded ready-to-use state only after the seal is broken.

8. The instrument according to claim 1, further comprising a registration member arranged on an outer side of the instrument for manual registration of one or more values determined with the instrument.

9. The instrument according to claim 8, wherein the registration member comprises a removable self-adhesive label.

10. The instrument according to claim 9, wherein the label is arranged at the position of the flow indicator, leaving a transparent window at the position of a display area of the flow indicator.

11. The instrument according to claim 1, further comprising a time duration indicator for determining a time duration of the urine flow.

12. The instrument according to claim 11, wherein the time duration indicator comprises a buffer reservoir in communication with the urine guide and the urine flow therethrough, and a collection reservoir in communication with the buffer reservoir through a defined passage opening, the collection reservoir further comprising a volume indicator for measuring a urine volume received therein, wherein during operation of the instrument, the defined passage opening allows through a fixed quantity of urine per unit of time from the buffer reservoir to the collection reservoir, so that the total volume of urine collected in the collection reservoir indicates the time duration of the urine flow.

13. The instrument according to claim 1, wherein the instrument is embodied as a disposable article that is formed substantially from flexible material.

14. The instrument according to claim 13, wherein the flexible material comprises at least two foil sheets hermetically attached to each other on a mutual contact surface while at least partially forming one or more of the receiving member, the urine guide, and the flow indicator.

15. The instrument according to claim 1, wherein in the expanded ready-to-use state the receiving member, urine guide, and flow indicator are substantially in line with each other.

16. The instrument according to claim 1, wherein the outflow openings are arranged in the side wall of the urine guide at mutually differing heights with respect to the outlet.

17. The instrument according to claim 1, wherein the outflow openings further comprise indicator paper for indicating the presence of at least one component of the composition of the urine flow.

18. The instrument according to claim 17, wherein the at least one component is glucose, bilirubin, ketones, blood, proteins, urobilinogen, nitrites, leucocytes or acids.

* * * * *